United States Patent
Kummer et al.

[11] Patent Number: 5,910,171
[45] Date of Patent: Jun. 8, 1999

[54] COMPONENTS FOR A MODULAR SHOULDER AND HIP PROSTHESIS

[75] Inventors: Frederick J. Kummer; Joseph D. Zuckerman, both of New York, N.Y.; Herve Jean Toggwiler; Laurent Marie Aubertot, both of Cedex, France

[73] Assignee: Hospital for Joint Diseases, New York, N.Y.

[21] Appl. No.: 08/579,021

[22] Filed: Dec. 15, 1995

Related U.S. Application Data

[63] Continuation-in-part of application No. 08/403,127, Mar. 13, 1995, abandoned, which is a continuation of application No. 08/031,220, Mar. 12, 1993, abandoned.

[51] Int. Cl.[6] .................................. A61F 2/30; A61F 2/40
[52] U.S. Cl. ................................................. 623/18; 623/19
[58] Field of Search ................................ 623/18, 19, 22, 623/23

[56] References Cited

U.S. PATENT DOCUMENTS

| | | | |
|---|---|---|---|
| 5,201,882 | 4/1993 | Paxson | 623/23 |
| 5,314,479 | 5/1994 | Rockwood, Jr. et al. | 623/19 |
| 5,336,368 | 8/1994 | Rispeter | 623/23 |
| 5,358,526 | 10/1994 | Tornier | 623/19 |
| 5,507,818 | 4/1996 | McLaughlin | 623/23 |

*Primary Examiner*—David J. Isabella
*Attorney, Agent, or Firm*—Stephen E. Feldman

[57] ABSTRACT

A head for a modular humeral (or hip) prosthesis which mates couplingly to a head mounting seat on the end of on elongated humeral stem is described. The head has an enganing syherical shaped outer surface which has a radius measured from a center which lies along an offset line which is inclined at an angle which ranges from between 10 to 30 degrees from the normal longitudinal axis of the elongated stem. The head has a longitudinal axis which is shifted form between 2.5 to 7.5 mm from a normal longitudinal axis. The elongated humeral stem includes a shaft seat which passes through the head mounting seat, which is adapted to receive a shaft extending from head. An adjustable to receive a shaft extending from the head. An adjustable interlocking alignment pin ensures desired orientation between the head and the head mounting seat during mating of the parts and maintains stability of orientation when mated.

7 Claims, 3 Drawing Sheets

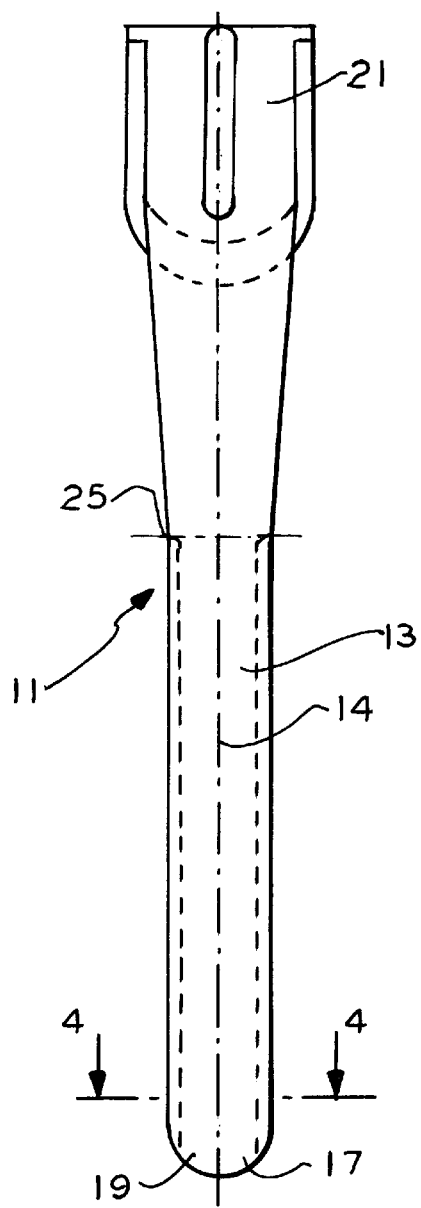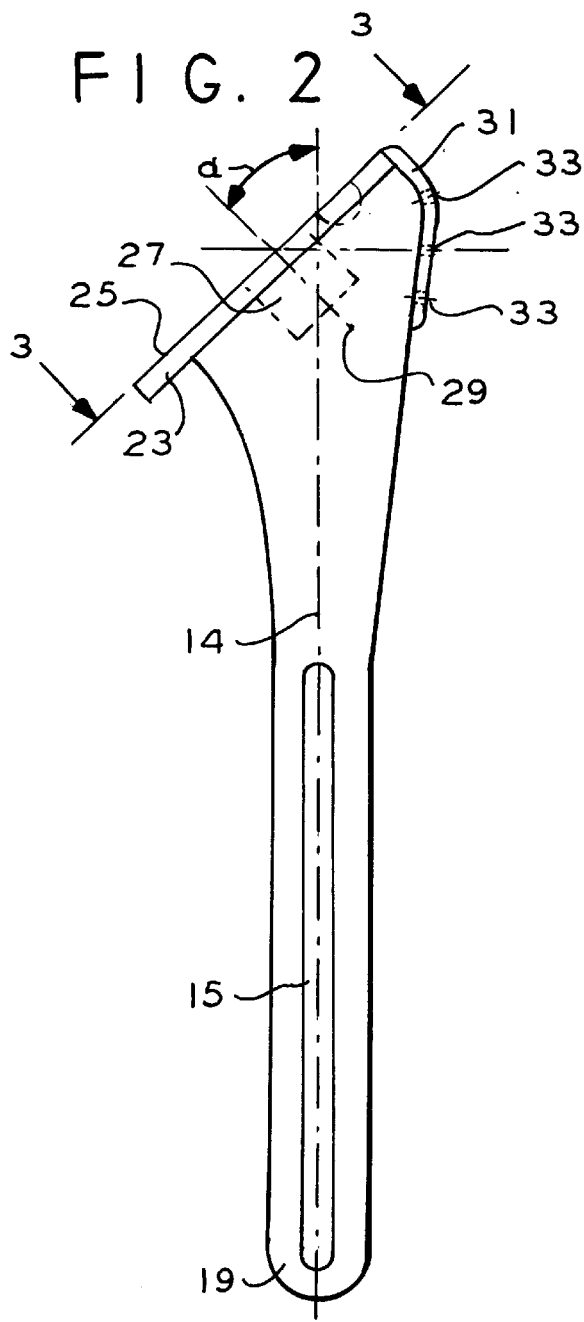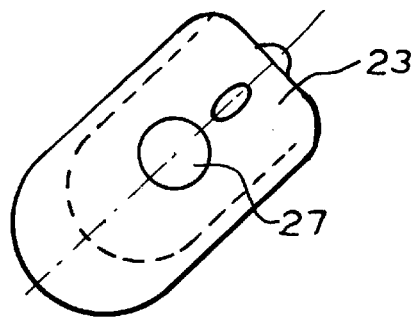

COMPONENTS FOR A MODULAR SHOULDER AND HIP PROSTHESIS

This application is a Continuation-in-part of U.S. patent application Ser. No. 08/403,127, filed Mar. 13, 1995, now abandoned, which is a Continuation of U.S. patent application Ser. No. 08/031,220, filed Mar. 12, 1993, now abandoned.

BACKGROUND OF THE INVENTION

1. Field of the Invention

The present invention particularly relates to components of a modular prosthesis for implantation in a ball and socket joint cavity of a body, with particular emphasis on load-bearing ball and socket joint replacement prosthesis.

2. Prior Art

A partial shoulder prosthesis is known to the art. These have included numerous design configurations of the various components, including the head, neck, collar, locking mechanisms and stein or shaft. Prostheses for use as a total shoulder replacement are also known and essentially comprise a humeral component which is implanted in the proximal humerus and a cup or articulating member implanted in the glenoid.

A number of different types of artificial shoulder joints have been heretofore proposed, and patent and other literature describing such joints are set forth below. However, it appears that designers of some of these artificial shoulders have used various porsthesis components, from other prosthesis art.

From a general standpoint, the shoulder joint is relatively unconstrained as compared to the hip. It includes a matching ball and socket, but the ball and socket members are held in their relative positions by a "rotator cuff" which includes a heavy layer of muscles and ligaments which surround the joint, however, in addition to providing security for the ball and socket members, this muscle and ligament structure also controls the overall movement of the arm, relative to the body. Although the shoulder has been referred to casually as a "non-weight bearing joint", the compressed force acting on the shoulder joint often reaches almost full body weight, especially when the arm, when supporting the body, is raised horizontally, medically referred to as 90 degrees abduction. Also, in the course of undertaking heavy work or athletic activities, the shoulder frequently carries loads substantially greater than the body weight. Therefore the shoulder must be considered a major load-bearing joint.

Corcerning terminology, the upper arm bone is the humerus, and the ball or rounded joint member at the upper end of t ie humerus fits into a socket in the shoulder bone, or scapula. The term "glenoid" refers to the aspect of the scapula which receives the humeral ball. Accordingly, the shoulder joint is sometimes referred to as the glenohunaral articulation.

Interlocking components which have been combined into a unit hive also been utilized in shoulder prosthesis with respect to both the glenoid component and the humeral component. Such a system is known as a modular prostheses. The prior art teaches the use of a partial shoulder prosthesis, wherein the humeral component has a modular design which enabled different available sized heads to be removably connected to a humeral stem member which has been implanted in the proximal humerus. The removable connection utilizes a coupling mechanism between the head and stem members, which can comprise a Morse taper. This permits the humeral head member to be inserted into the stem member through a neck portion, the neck portion which fits into the stem member such as disclosed by Dines et al in U.S. Pat. No. 4,865,605. Alteratively, the stem may be constructed to be inserted into an opening in the head, or an intermediate element may be tapered on both sides to be inserted into both the head and the stem simultaneously.

An article "The Geometry Of The Humeral Head And The Design Of Prosthesis" by Roberts et al. in The Journal Of Bone And Joint Surgery dated July 1991 provides a dimensional analysis of approximately 30 cadaveric humeri. The summary states, "The articular surface of the humeral head is usually described as facing posteromedial, making an angle of between 16 degrees and 35 degrees wish the transepicondylar plane. At hemiarthroplasty, the articular surface also appears to be offset posteriorly with respect to the humeral shaft. Coracoid impingement may occur if this offset is not accommodated. An analysis was made of 20 cadaveric humeri using an industrial co-ordinate measuring machine. The position of the center of the head was defined with respect to the humeral shaft and transepicondylar plane. The humeral articular surface was found to be retroverted by 21.4 degrees and its center offset posteriorly by 4.7 mm.

Previous interpretation of retroversion did not take into account the posterior displacement, and this mat be of importance in improving future prosthetic design."

Hip prosthesis are also known in the art and these have also included various design configurations. Gustilo et al. in U.S. Pat. Reissue No. 32,488 discloses a neck member connecting a spherical head to the shaft member through a collar. The neck member is anteverted with respect to the collar at an angle of about 10 to 20 degrees. Stossell, in U.S. Pat. No. 4,944,764, discloses a head having a center which is offset by no more than 4.25 cm from the longitudinal axis of the shaft or stem member, to minimize damage to the patient during insertion of the prosthesis.

The U.S. Pat. No. 5,314,479, issued to Rockwood, et al teaches a four element modular shoulder prosthesis which has a three element stem which is screwed together for receiving a head for inserting into the socket cavity. The head, the fourth element, is radially symmetrical with a seating shaft that may be offset from the center of the head. The seating shaft, which has a limiting shoulder, includes a six position locking element at the end thereof, to prevent rotational movement of the head, when seated. The. locking element, however, is positioned at a major stress point and is subject to stripping or rupture.

SUMMARY OF THE INVENTION

Objects of the Invention

An object of the present invention is to provide an improved head member that more closely approximates the normal physiological anatomy than existing devices.

Another object of the present invention is to provide a head member which allows the head member to be selectively adjusted and/or rotated about the humeral stem member, into a defined position, to accommodate the particular requirements of the patient.

A further object of the present invention is to provide an improved head member for a modular humeral prosthesis which head member cones in different configurations and sizes.

These and other objects and advantages of the present invention are achieved when practicing one of the broader aspects of the present. invention in which a head for a multi-part prosthetic device having an elongated stem means, which has a longitudinal axis and a mounting means for connecting the head to the stem means, the mounting means having a nominal longitudinal axis which is offset from the longitudinal axis of the stem means by a predetermined angle. The head has an engaging spherical shaped outer surface. The spherical shaped outer surface has a radius (20–30 mm) from a center, which lies along an offset line inclined at an angle which ranges from between 10 and 30 degrees from the nominal longitudinal axis of the mounting means. The mounting means and the head mounting means or head mounting shaft can also have a longitudinal axis which is offset a distance which ranges from between 10 to 30 degrees from the nominal longitudinal axis of the mounting means. The mounting means and the head mounting mens or head mounting shaft can also have a longitudinal axis which is offset a distance, which ranges from between 2.5 to 7.5 mm from the nominal longitudinal axis. The. nominal longitudinal axis of the mounting means and the head mounting means or head mounting shaft are identical and are defined by and is the same as the longitudinal axis of the head mounting means or head mounting portion of a conventional head or cup member.

Other aspects of the invention relate more generally to multi-part prostatic devices usable in the ball and socket joint environment of the body. From one of these aspects the invention provides adjustable interlocking apparatus for selectively orienting the companion parts of the multi-part prosthetic device into a predetermined, selectable relationship between such parts, during assembly. From another of these aspects, the invention provides interlocking apparatus for maintaining positive orientational stability between assembled parts of the prosthetic device when the prosthetic device is in its assembled form thus maintaining assured insitu stability between assembled parts of the multi-part prosthetic device when implanted in a joint cavity environment.

These and other features and advantages of the present invention will be described in connection with the preferred embodiment of the invention with reference to the attached drawings, wherein:

BRIEF DESCRIPTION OF THE DRAWINGS

FIG. 1 represents in back or lateral view the stem portion of a humeral component according to the present invention;

FIG. 2 represents, in side view the invention represented in FIG. 1;

FIG. 3 represents, in top view, the invention represented in FIG. 1 of FIG. 2;

FIG. 4 represents, in sectional view the invention along line 4—4 of FIG. 1;

DETAILED DESCRIPTION OF THE INVENTION

Figure 5:
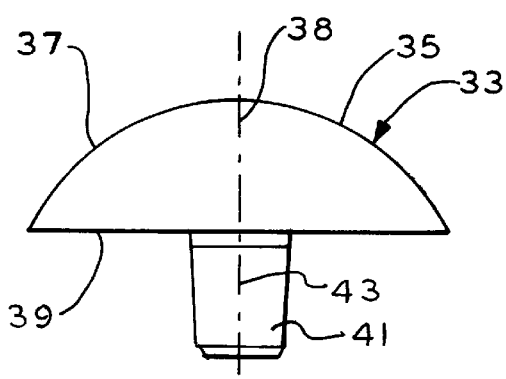
FIG. 5 represents, in side view a prior art head portion of a humeral component.

Referring now to FIGS. 1–4, a modular humeral component, according to the present invention, comprises a humeral stem means or stem 11 having an elongated portion 13. Elongated portion 13 has a longitudinal axis 14 and opposed, elongated, recesses 15 on both sides of the elongated portion. The recesses 15 aid in the fixation of the stem 11 in the humerus and provide stability against rotation of the stem.

The distal end 17 of the stem 11 has a rounded portion 19 and the proximate end 21 of the stem 11 has a support surface 23. The support surface 23 extends radially from the stem 11. The support surface 23 has an upper planar surface 25 and a bore 27 extending inwardly from the upper planar surface 25. The bore or humeral stem mounting means or humeral stem bore 27 comprises one portion of a mounting means subsequently discussed, and has a longitudinal axis 29 which is offset from the longitudinal axis 14 of the elongated portion 13 of the stem 11. The offset is a predetermined angle "a", which, in the preferred embodiment is 45 degrees. Similarly the upper planar surface 25 of the support surface 23 is at a predetermined angle "a" from the same longitudinal axis 14, and is preferable 45 degrees. The stem 11 also includes a flange portion 31 having fixation apertures 33 which serve to aid in the fixation of the implant after being imbedded in the humerus.

Accordingly, the longitudinal axis 29 of the bore or stem mounting means 27 is inclined from the longitudinal axis 14 of the stem 11 by the offset angle "a", which as indicated previously is preferably 45 degrees. Furthermore, both the support surface 23 and its upper planar surface 25 are Inclined from the longitudinal axis 14 of the stem 11 by the same offset angle "a". The support surface 23 and its upper planar surface 25 are consequently disposed perpendicular to the longitudinal axis 29. The bore or stem mounting means 27 which extends inward from the upper planar surface 25 through the support surface 23 has a longitudinal axis 29, which in the present invention is coincident with the "nominal" longitudinal axis 29 of the bore or stem mounting means 27 is also offset from the longitudinal axis 14 of the stem 11 by the offset angle "a", which as previously indicated is a predetermined angle of 45 degrees, for example.

Referring now to FIG. 5, a conventional head or cup member or articulating member or head means 33 is illustrated, which has a spherical shaped outer surface 35 entirely around the outside surface 37 of the head 33, a central axis 38 of the spherical shaped outer surface 35, and a lower planar surface 39. A tapered cylindrical mounting lock means or head mounting shaft or head mounting means 41 protrudes downward from the center of the lower planar surface 39 of the head 33, and is preferably integrally formed together with the head 33a, and in this invention is disposed such that the longitudinal axis 43 of the mounting lock means 41 is coincident with the longitudinal axis 29 of the bore 27. The longitudinal axis 29 of the bore 27 is offset from the longitudinal axis 14 of the elongated portion 13 of the stem 11 by a predetermined angle "a", which as indicated previously is 45 degrees. Similarly the longitudinal axis 43 of the mounting lock means 41 is coincident with the central axis 38 of the spherical shaped outer surface 35 of the head 33. The mounting means comprised, in addition to the humeral stem mounting means or humeral stem bore 27 formed in the stem 11, the head mounting means or head mounting shaft or mounting lock means 41, which when inserted into the bore 27 provide a tight fit. The mounting lock means 41 and bore 27 are preferably in the form of conventional Morse male and female taper locks, respectively, which provide a friction fit when connected together. When so connected, the lower planar surface 39 of the head 33 abuts against the upper planar surface 25 of the stem 11.

The "nominal" longitudinal axis of the mounting means and the head mounting means or mounting lock means 41 are identical and is defined by and is the same as the longitudinal axis 43 of the mounting lock means 41. Accordingly, the nominal longitudinal axis as used herein is inclined from the longitudinal axis 14 of the stem 11 by the offset angle "a", which as indicated previously is preferably 45 degrees. Furthermore, the lower planar surface 39 of the head 33, and both the support surface 23 and its upper planar surface 25 of the stem 11, are inclined from the longitudinal axis 14 of the stem 11 by the offset angle "a". Consequently, these surfaces 39, 23 and 25 are all disposed perpendicular to the nominal longitudinal axis or longitudinal axis 43 of the mounting lock means 41. The bore or stem mounting means 27 which extends inward from the support surface 23 and its upper planar surface has a longitudinal axis 29, which in the present invention is coincident with the nominal longitudinal axis 43; therefore, the longitudinal axis 14 of the stem 11 by the offset angle "a", which as previously indicated is a predetermined angle, and in this embodiment 45 degrees.

The spherical shaped outer surface 35 of head 33 is adapted to engage the glenoid cavity itself or its equivalent in a prosthesis. The spherical surface 35 has a radius from a center which lies along its central axis 38. In this illustrated conventional head 33 the radius is 25 mm long.

Figure 6:
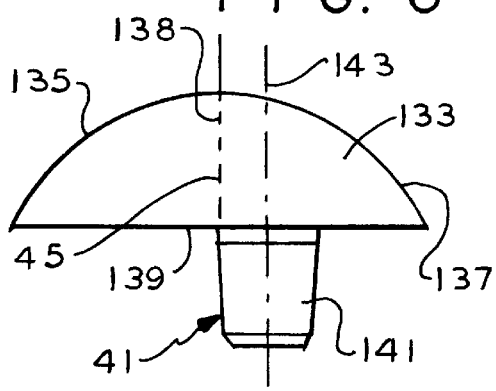
FIG. 6 represents, in side view, a first embodiment of the head portion of a humeral component according to the present invention and its relationship to the prior art head portion of FIG. 5 which is shown in dotted lines.

Referring now to FIG. 6 wherein a first embodiment of the head or head means 133 of the present invention is shown in solid lines. and wherein the mounting lock means 41 of the conventional head 33 is shown in dotted lines for comparison purposes. the head 133 has an outside surface 137 which is completely in the form of spherical shaped outer surface 135, a central axis 138 of the spherical shaped outer surface 135, and a lower planar surface 139. A tapered mounting lock means 141 protrudes downward from the lower planar surface 139 of the head 133, and is preferably integrally formed together with the head 133. The lock means 141 is disposed such that the longitudinal axis 143 of the mounting lock means 41. This offset distance can arrange from between 2.5 to 7.5 mm from the nominal longitudinal axis 43 of the mounting lock means 41. The mounting means comprises, in addition to the bore 27 formed in the stem 11,. the mounting lock means 141, which when inserted into the bore 27 provides a tight fit. The mounting lock means 141 and bore 27 are preferably in the form of conventional Morse male and female respectively, taper locks, which provide a friction fit when connected together. When so connected, the lower planar surface 139 of the head 133 abuts against the upper planar surface 25 of the stem 11.

The spherical shaped outer surface 135 of head 133 has as radius from a center which lies along its central axis 138, and is coincident with-the nominal longitudinal axis 43 of the mounting lock means 41. In this embodiment the radius is preferably 25 mm long.

Figure 7:
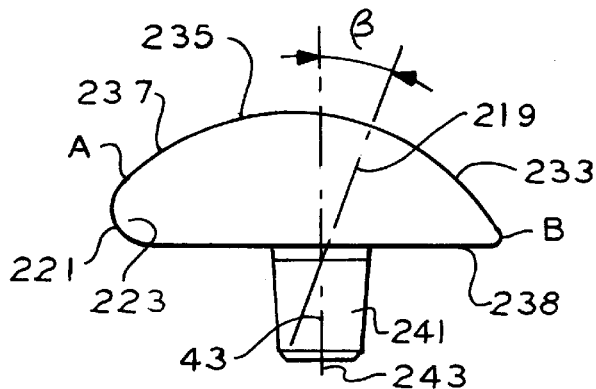
FIG. 7 represents, in side view, a first version of a second embodiment of the head portion of a humeral component according to the present invention.

Referring now to FIG. 7, wherein a second embodiment of the head or head means 233 of the present invention is illustrated. The head 233 has an outside surface 237 having a smooth outer surface 221 on the inner edge 223 of the head 233, and a spherical shaped outer surface 235 extending from point A at the upper end of the inner edge 223 to point B at the outer edge of a lower planar surface 239. A tapered lock means 241 protrudes downward from and is perpendicular to the lower planar surface 239 of the head 233 and is preferably integrally formed together with the head 233. The tapered.lock means 241 is disposed such that its longitudinal axis 243 is located approximately at the center of the lower planar surface 239. The longitudinal axis 243 is coincident with or nearly coincident with the nominal longitudinal axis 43 of the mounting lock means 41. The central axis of the spherical shaped outer surface 235 lies along an offset line 219 which is inclined at an angle "B" from the nominal longitudinal axis 43 of the mounting locking means 41 (or in this case at an angle "B" from the longitudinal axis 243 of the mounting locking means 241). The angle "B" is preferably about 20 degrees but can range from between 10 and 30 degrees. In this embodiment the radius of the spherical shaped outer surface 235 is preferably 25 mm long.

The mounting means comprised, in addition to the bore 27 formed in the stem 11, the mounting lock means 241, which when inserted into the bore 27 provides a tight fit. The mounting lock means 241 and bore 27 are preferably tapered, the form of a conventional male and female Morse taper, which provide a friction lock when the male is inserted into the female. When so connected, the lower planar surface 239 of the head 233 abuts against the upper planar surface 25 of stem 11.

Figure 8:
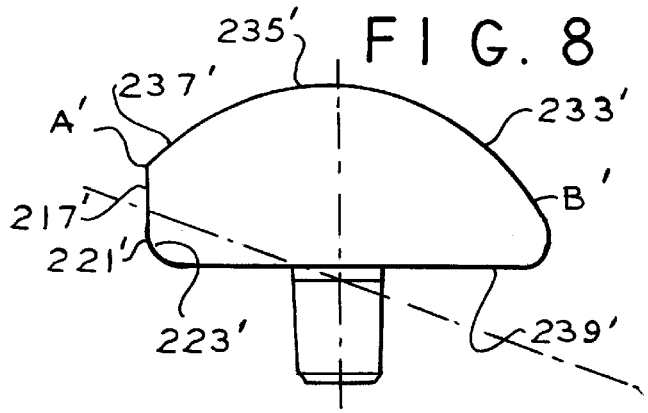
FIG. 8 represents, in side view, a second version of the second embodiment of the head portion of a humeral component according to the. present invention.

Referring now to FIG. 8 wherein a second version of the second embodiment of the head or head means 233 is illustrated; it is noted that its design is almost the same as the first version shown in FIG. 7 and accordingly only some of its differences are described. The head 233' has an outside surface 237' having a smooth outer surface 221' on its inner edge 223' of the head 233', and a spherical shaped outer surface 235' extending from point A' at the upper end of the inner edge 223' to point B' just above the outer edge of the lower planar surface 239'. The smooth outer surface 221' includes a relatively long straight portion 217' between the short upper and lower curved portions.

Figure 9:
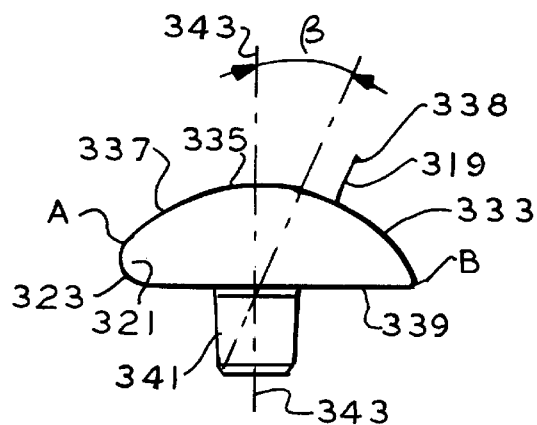
FIG. 9 represents, in side view, a first version of a third embodiment of the head portion of a humeral component according to the present invention.

Referring now to FIG. 9 wherein a third embodiment of the head or head means 333 of the present invention is illustrated; this embodiment combines the features contained in the first and second embodiments. The head 333 has an outer surface 337 having a smooth outer surface 321 on the inner edge 323 of the head 333 and a spherical shaped outer surface 335 extending from point A at the upper end of the inner edge 323 to point B at the outer edge of a lower planar surface 339. A tapered mounting lock means 341 protrudes downward from the lower planar surface 339 of head 333, and is preferably integrally formed together with the head 333 and is dispose such that the longitudinal axis 343 of the mounting lock means 341 is offset a distance of preferably, approximately, 5 mm from the nominal longitudinal axis 43 of the mounting lock means 41 (FIG. 6). The offset distance can range from between 2.5 to 7.5 mm from the nominal longitudinal axis 43 of the mounting lock means. The central axis 338 of the spherical shaped outer surface 335 lies along an offset line 319 which is inclined at an angle "B" from the nominal longitudinal axis 43 of the mounting locking means 41 (or shown, at an angle "B" from the longitudinal axis 343). This angle "E" is preferably about 20 degrees but can range from between 10 and 30 degrees.

In this embodiment, the radius of the spherical shaped outer surface 335 is preferably 25 mm long.

The mounting means comprises, in addition to the bore 27 formed in the stem 11, the mounting lock means 341, which when inserted into the bore 27 are preferably in the form of a conventional Morse male and female, respectively, taper locks, which provide a friction fit when connected together. When so connected, the lower planar surface 339 of the head 333 abut against the upper planner surface 25 of stem 11.

Figure 10:
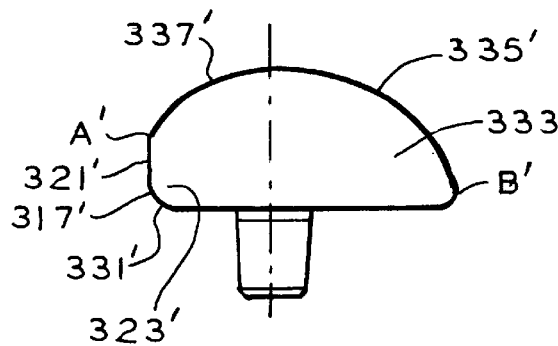
FIG. 10 represents, in side view, a second version of the third embodiment of the head portion of a humeral component according to the present invention.

Referring now to FIG. 10 wherein a second version of the third embodiment of the head 333 is illustrated; it is noted that its design is almost the same as the first version shown in FIG. 9 and accordingly only some of the differences are described. The head 333' has an outside surface 337' having a smooth surface 331' on its inner edge 323' of the head 333', and a spherical shaped outer surface 335' extending from the point A' at the upper end of the inner edge 323' to point B' just above the outer edge of ten lower planar surface 339'. The smooth outer surface 321' includes a relatively long straight portion 317' between the short upper and lower curved portions.

The head or head means is suitable for use in a modular hip joint prosthetic and its spherical shaped outer surface is adapted to engage an acetabular bearing member or its equivalent in a prosthetic replacement.

The preferred embodiment of the present invention is represented with the structure of the locking means, which locks the head onto the stem, including a tapered head mounting shaft, such as 41 in FIG. 6, for example, and a mating seat, in the form of a tapered hole such as 27 in FIG. 2, for example, with the protrusion or shaft formed integrally with the head. The mating tapered structures provides for unlimited arcuate positioning, or orientation, between the head and the stem and when assembled provides rotational stability by friction between the shaft and the seat because of the tapered parts.

However, it may be desirable to provide a means for ensuring that the mating parts of a multi-part prosthesis are guided into a predetermined relationship, or orientation during assembly of the parts and that positive orintational stability between the assembled parts is maintained at all times during the time the parts are coupled. This is accomplished by another aspect of the present invention which provides for a mutually interlocking assembly which guides the mating parts into a predetermined orientation, relative to each other, as the mating parts of the prosthesis are assembled and, after the parts have been assembled, the mutually interlocking assembly maintains the mated parts in such predetermined orientation providing positive stability of the mated parts, relative to such predetermined orientation, during assembly.

Figure 11:
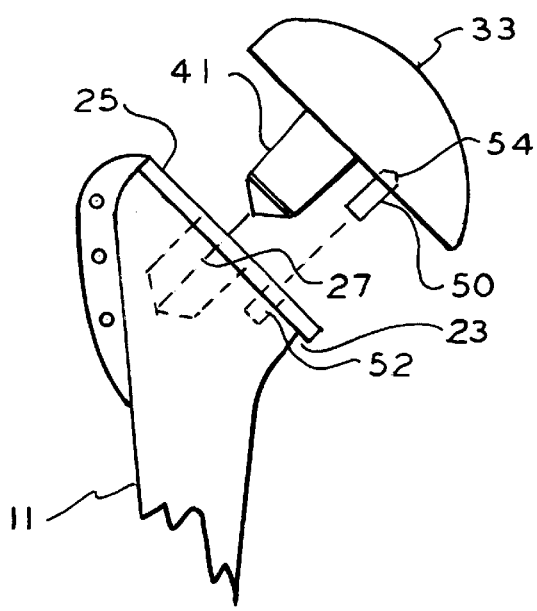
FIG. 11 represents, another aspect of the invention in preferred embodiment.
Figure 12:
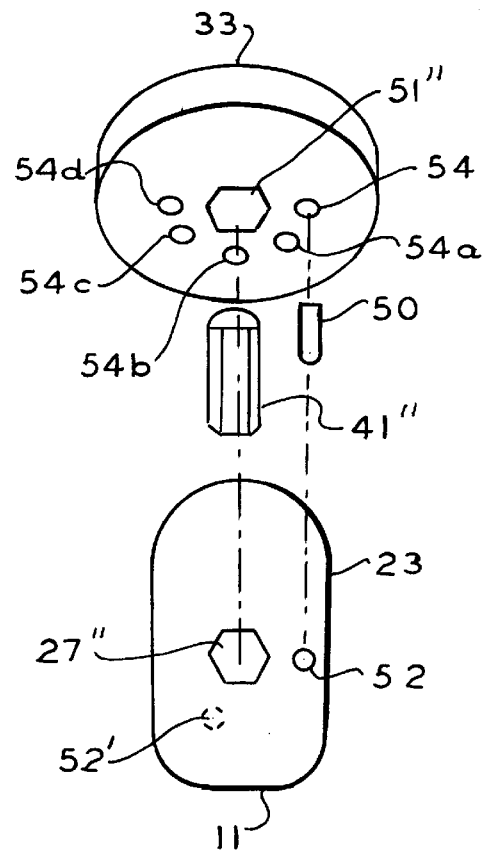
FIGS. 12, 13, 14 and 15 represent alternate embodiments of the aspect of the invention represented in FIG. 11.
Figure 13:
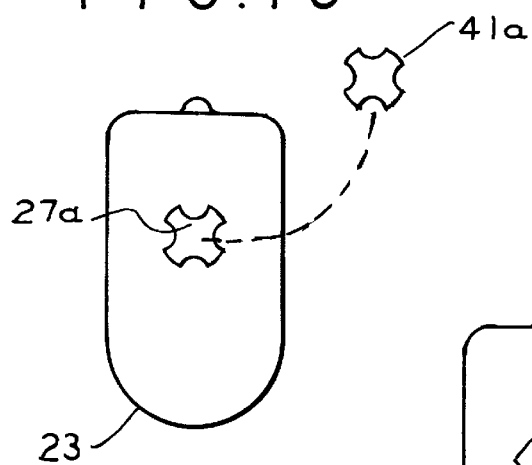

These additional aspects of the invention-are provided by interlocking apparatus some of which are represented in FIGS. 11, 12 and 13.

Accordingly, FIG. 11 represents the head 33 with a head mounting shaft 41, integral with the head, which may be tapered, for example, and a stem 11 with a tapered bore seat 27, for example. The head 33 includes one or more holes 54, which may have parallel walls, located about the central axis of the shaft 41 for receiving a pin 50, which preferable has parallel walls. The stem 11 also includes a hole 52, which may, according to the arcuate relationship between the head and the stem, align with the hole 54. The hole 52 is adapted to receive the pin 50. The location of the hole 54 in the head and the location of the hole 52 in the stem may be such that when the head and the stem are assembled, the holes 54 and 52 will be in axial alignment when the head and the stem are in a predetermined arcuate relationship, for example, at zero (0) degrees of arcuate offset. A predetermined arcuate offset is assured by assembling the head on to the stem with the pin 50 in the holes 54 and 52. In addition, assembly of the head on to the stem with the pin 50 in the holes 54 and 52, assures positive rotational stability between the head and stem.

FIG. 12 represents that several pin securing holes, such as 54, 54a, 54b, 54c and 54d may be provided on the head, in spaced, arcuate relationship about the central axis of the shaft 41 of FIG. 11 so as to permit selectable, predetermined positioning of the head on to the stem. Pin receiving holes such as represented at 54, 54a, 54b, 54c and 54d in FIG. 12 may be on the head 33 represented in FIG. 11, as well. The holes may be offset from each other some 45 degrees, for example, so that positioning of the head, relative to the stem may be and in predetermined increments, such as 45 degrees for example. To increase the arcuate selectability and adjustability between the head and the stem during assembly, and retention of rotational stability between the head and stem after assembly, a hole 52', shown in broken line form, may be positioned in the stem, offset from the hole 52, so that the incremental degree of adjustment at assembly between the head and stem may be reduced from 45 degrees to 22.5 degrees, effectively increasing selectability in positioning.

By inserting the pin 50 in a selected receiving hole in the head and assembling the head on to the stem so that the shaft 41 seats in the bore seat 27 and the pin 50 aligns with and seats in a selected hole in the stem, for example 52, predetermined, selective positioning of the head and stem is assured at assembly and rotational stability between the head and stem is assured after assembly.

FIG. 12 also represents that the shaft 41", which in the preferred embodiment is integral with the head, may be an independent, removable shaft. In such structure the head 33 would have a shaft receiving bore 51". The receiving bore 51" is represented as hexagon in shape. The removable shaft 41" is represented in a compatible shape as is the bore seat 27" in the stem 11.

The compatible geometric structure of the interior of the shaft receiving bore 51", the interior of the bore seat 27' and the shaft 41" provide for selective positioning of the head on the stem during the assembly operation and positive stability of the rotational relationship between the head and the stem during the assembled period.

Figure 14:
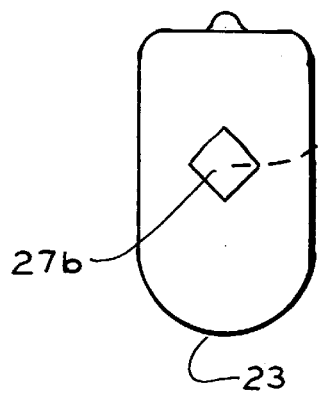
Figure 15:
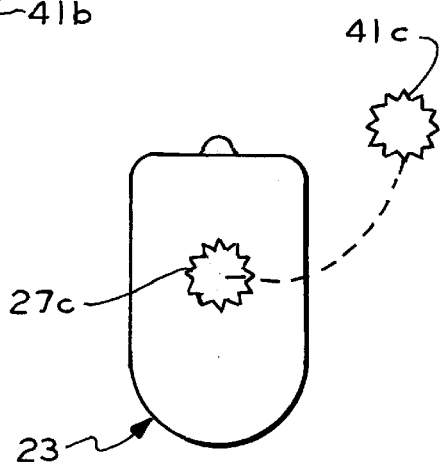

FIGS. 13, 14 and 15 represent alternate geometric structures for the shafts and the bore seats. FIG. 13 represents that each component may be structured with compatible fluting, the shaft 41a has external fluting and the seat 21a has internal fluting.

FIG. 14 represents that the mounting shaft 41b may have a rectangular geometric shape while the bore seat 27b has a comparable rectangular configuration.

FIG. 15 represents that the geometric configuration of the mounting shaft 41c may be a multi-toothed configuration, in some respects resembling a gear, while the bore seat 27c has a comparable gear-like configuration. This configuration provides multiple head to stem arcuate position selection for assembly and positive rotational stability between the head and the stem during the assembled period. The several embodiments of geometric configuration of the mounting assembly is not meant to be limiting.

It will be appreciated that the instant specification and claims are set forth by way of illustration and not limitations, and that various modifications and changes may be made without departing from the spirit and scope of the present invention.

What is claimed is:

1. A prosthetic device for implanting in a ball and socket joint cavity of a patient comprising:

an enlongate stem having a longitudinal axis, a distal end and an opposite head end, said head end terminating in a generally flat surface with an elongate mounting lock bore formed therein, said mounting lock bore extending generally perpendicular to said flat surface of said stem;

an articulating head member having a generally curved articulating surface and an opposite generally flat planar surface, said head member including a generally elongate mounting lock member extending perpendicular from said planar surface and offsert from a central axis of said articulating head member, said device further including a plurality of bores extending generally perpendicular into said planar surface about said elongate mounting lock member and at least one bore extending generally perpendicular into said flat surface; and a pin element configured to be insertable into axially aligned said at least one bore and one of said plurality of said bores which allows customized orientation of the head member with respect to the stem to meet the anatomical requirement of the patient.

2. The prosthetic device of claim 1 wherein said generally flat planar surface is disposed at an angle of about 45 degrees relative to said longitudinal axis of said stem.

3. The prosthetic device of claim 1 wherein said offset is a distance of about 2.5 cm to about 7.5 cm.

4. The prosthetic device of claim 1 wherein said offset is a distance of about 5.0 cm.

5. The prosthetic device of claim 1 wherein said longitudinal axis of the stem is offset from said central axis of said head member at an angle from about 10 degrees to about 30 degrees.

6. The prosthetic device of claim 1 wherein a longitudinal axis of the stem is offset from said central axis of said head member at an angle of about 20 degrees.

7. The prosthetic device of claim 1 wherein said lock bore and each of said plurality of bores are configured to provide an angle of about 22.5 degrees to about 45 degrees between said longitudinal axis of said stem and said central axis of said head member.

* * * * *